(12) United States Patent
Clevenger et al.

(10) Patent No.: US 11,457,811 B2
(45) Date of Patent: Oct. 4, 2022

(54) SYSTEMS AND METHODS FOR DETERMINING FACILITY EXPOSURE TO A SOURCE CONDITION

(71) Applicant: ZEBRA TECHNOLOGIES CORPORATION, Lincolnshire, IL (US)

(72) Inventors: Nathan J. Clevenger, Burnsville, MN (US); Scott R. Olson, St. Paul, MN (US); Dino O. Gregorich, Alexandria, VA (US); Matthew Louis Kowalski, Merrick, NY (US)

(73) Assignee: Zebra Technologies Corporation, Lincolnshire, IL (US)

( * ) Notice: Subject to any disclaimer, the term of this patent is extended or adjusted under 35 U.S.C. 154(b) by 280 days.

(21) Appl. No.: 16/906,173

(22) Filed: Jun. 19, 2020

(65) Prior Publication Data

US 2021/0393129 A1    Dec. 23, 2021

(51) Int. Cl.
*A61B 5/00*      (2006.01)
*H04W 64/00*   (2009.01)
*H04W 4/029*   (2018.01)

(52) U.S. Cl.
CPC .......... *A61B 5/0022* (2013.01); *A61B 5/7275* (2013.01); *H04W 4/029* (2018.02); *H04W 64/003* (2013.01)

(58) Field of Classification Search
CPC ... A61B 5/0022; A61B 5/7275; H04W 4/029; H04W 64/003
USPC .......................................................... 705/3
See application file for complete search history.

(56) References Cited

U.S. PATENT DOCUMENTS

| | | | |
|---|---|---|---|
| 11,290,282 B2 * | 3/2022 | Heurich | H04L 63/08 |
| 2009/0325535 A1 * | 12/2009 | Felt | H04W 4/90 |
| | | | 455/404.1 |
| 2019/0373469 A1 * | 12/2019 | Bradley | H04L 63/061 |

* cited by examiner

*Primary Examiner* — Rownak Islam (57) ABSTRACT

A method includes: obtaining, at a server, a diagnosis key published by a tracing service, the diagnosis key associated with a source device; identifying one or more detected proximity identifiers associated with the diagnosis key; identifying one or more affected network detection devices associated with the one or more detected proximity identifiers; retrieving, from a repository, device data for the one or more affected network devices, the device data identifying a facility of the one or more affected network devices; and generating facility exposure data for the facility, the facility exposure data defining exposure associated with the source device at the facility.

20 Claims, 7 Drawing Sheets

SYSTEMS AND METHODS FOR DETERMINING FACILITY EXPOSURE TO A SOURCE CONDITION

BACKGROUND

Contact tracing systems may enable individual mobile device owners to be notified of potential exposure to conditions such as infectious diseases. Such systems may be inaccessible to operators of mobile devices selected from shared device fleets, however.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

Contact tracing allows identifications of individuals who have been in contact with, for example, by being within close proximity of, an identified individual or source condition. Contact tracing is particularly applicable, for example, when an individual is identified as carrying an infectious and communicable disease. Contact tracing may then be employed to identify other individuals who may have been infected and/or who may be required to take additional protective measures or precautions prior to diagnosis.

Current solutions for contact tracing may leverage the ubiquity of mobile devices to facilitate identification of contacts from an index case. Some contact tracing mechanisms, such as the Privacy-Preserving Exposure Notification developed by Apple Inc. and Google LLC employ cryptographic methods allowing end users to be notified of potential exposure to a diagnosed user, while preserving the anonymity of the diagnosed users. These mechanisms are based on individual tracking and do not provide a facility- or enterprise-wide notification of potential exposures. Further, the mere identification of an infected individual in a facility does not allow for identification of individual employees or operators working in the facility who may have been in close proximity to the infected individual, and hence further contact tracing is restricted.

Examples disclosed herein are directed to a method comprising: obtaining, at a server, a diagnosis key published by a tracing service, the diagnosis key associated with a source device; identifying one or more detected proximity identifiers associated with the diagnosis key; identifying one or more affected network detection devices associated with the one or more detected proximity identifiers; retrieving, from a repository, device data for the one or more affected network devices, the device data identifying a facility of the one or more affected network devices; generating facility exposure data for the facility, the facility exposure data defining exposure associated with the source device at the facility.

Additional examples disclosed herein are directed to a server comprising: a memory; and a processor connected with the memory, the processor configured to: obtain a diagnosis key published by a tracing service, the diagnosis key associated with a source device; identify one or more detected proximity identifiers associated with the diagnosis key; identify one or more affected network detection devices associated with the one or more detected proximity identifiers; retrieve, from a repository connected to the server, device data for the one or more affected network devices, the device data identifying a facility of the one or more affected network devices; generate facility exposure data for the facility, the facility exposure data defining exposure associated with the source device at the facility.

Additional examples disclosed herein are directed to a non-transitory computer-readable medium storing a plurality of computer-readable instructions executable by a processor, wherein execution of the instructions configures the processor to: obtain a diagnosis key published by a tracing service, the diagnosis key associated with source device; identify one or more detected proximity identifiers associated with the diagnosis key; identify one or more affected network detection devices associated with the one or more detected proximity identifiers; retrieve, from a repository connected to the server, device data for the one or more affected network devices, the device data identifying a facility of the one or more affected network devices; generate facility exposure data for the facility, the facility exposure data defining exposure associated with the source device at the facility.

Figure 1:
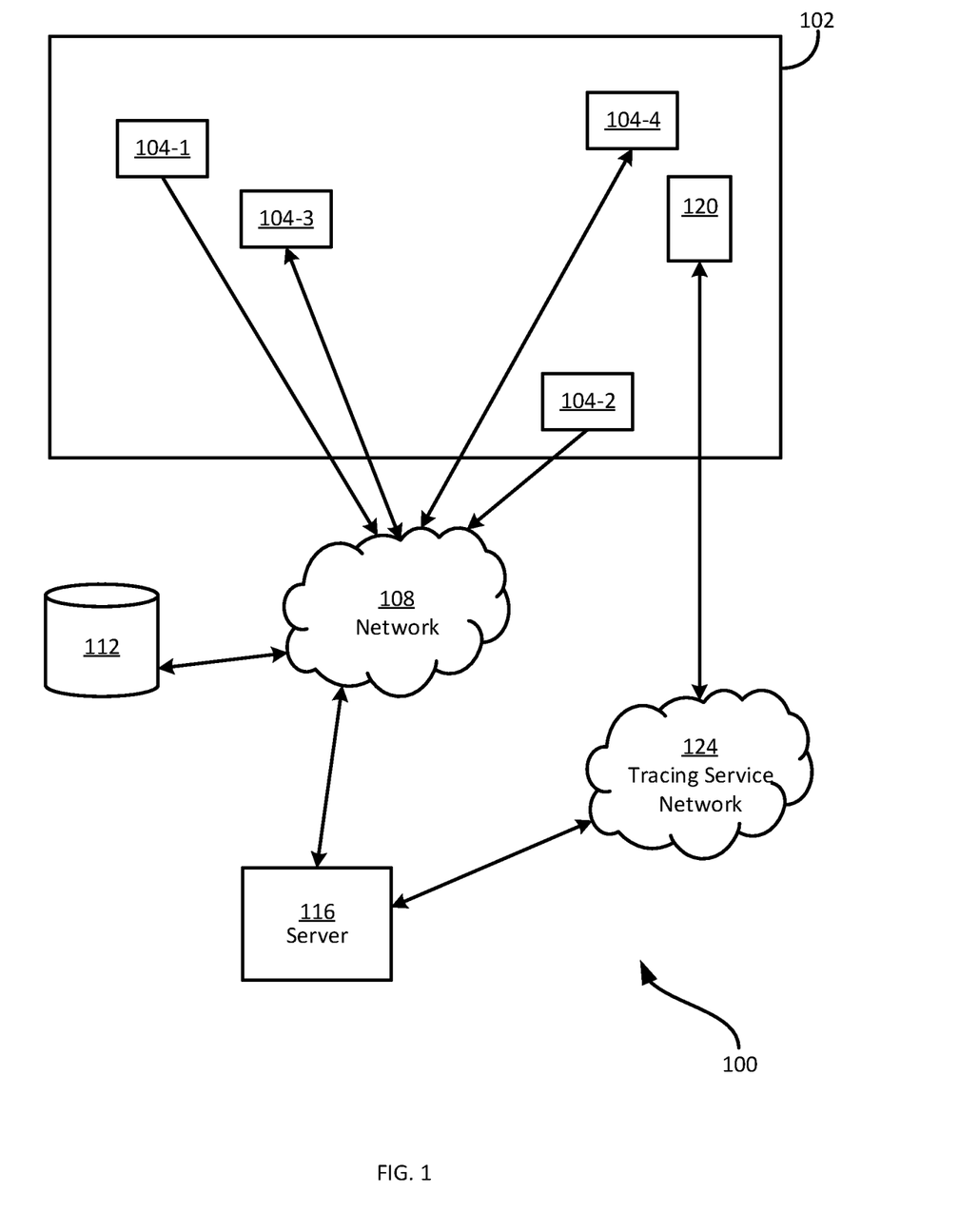
FIG. 1 is a schematic of a system for determining facility exposure to a source condition.

FIG. 1 depicts a system 100 for determining facility exposure to a source condition. The system 100 may be deployed in association with at least one facility 102, such as a retail establishment, warehouse, event space, commercial or government building, or other facility. As will be apparent in the discussion below, the system 100 may also be deployed in a wide variety of other types of facilities. The system 100 includes network detection devices 104, a network 108, a network repository 112, a server 116, a source device 120, and a tracing service network 124.

Generally, the system 100 provides facility exposure data to identify specific devices, operators, or spaces in a facility that may have been affected by (e.g., in close proximity to) a source condition, based on proximity to a source device (i.e., used by an infected individual). The system 100 leverages anonymous, privacy-preserving contact tracing mechanisms and services and integrates them with facility-based data tracking and analysis infrastructure to provide enhanced contact tracing. In particular, the facility-based data tracking and analysis infrastructure detects and tracks nearby devices executing a contact tracing application, and hence can identify historical locations of a diagnosed individual (based on their mobile device) in a facility. The facility and enterprise specific information tracked in the system 100 further allows for identification of specific potentially affected operators and devices in the facility, as well as subsequent facility-based contact tracing.

The network detection devices 104, of which four examples, 104-1, 104-2, 104-3, and 104-4 are depicted (collectively referred to as the network detection devices 104 and generically referred to as a network detection device 104), may be located around the facility 102 and are generally configured to support the operational data tracking and analysis infrastructure in the facility 102. The network detection devices 104 may include fixed sensors, such as monitoring devices, including environmental sensors (e.g., temperature sensors or the like), image sensors (i.e., cameras), barcode scanners, and other suitable devices that are fixed in the infrastructure of the facility 102. The network detection devices 104 may also include mobile computing devices such as handheld computers, barcode scanners, tablets, or the like, which may be moved and operated by operators in the facility. The network detection devices 104 can further include stationary computing devices, such as a desktop computer deployed within the facility.

The network detection devices 104 generate streams of detection data containing measurement data, image data, barcode data, and other data (in accordance with the type of each network detection device 104) captured or detected at the network detection device 104. The detection data may include a measurement or other data (e.g., a temperature measurement, a decoded barcode, a location, other detected data, or the like), as well as a timestamp indicating the date and time the data was captured. The detection data may also include a network detection device identifier, such as a serial number of the network detection device 104 that generated the detection data. Various other attributes may also be contained in the detection data, such as a location of the corresponding network detection device 104 within the facility at the time the data was captured, for example, if the network detection device 104 is a mobile device, and the like.

Some network detection devices 104, such as a mobile computing device, a portable barcode scanner, or the like, may be operated by an operator or worker in the facility for the duration of the operator's working shift. Accordingly, the operator may sign into the device, for example, using an operator identifier (e.g., a login name, employee number, or the like) and optionally, a password. The network detection device 104 may therefore generate account data associating the operator identifier with the network detection device identifier. The account data may further include a timestamp indicating the date and time of an account event (e.g., logging into or out of) occurring at the network detection device 104.

The network detection devices 104 are further configured to detect other nearby network detection devices 104, in accordance with the data tracking and analysis network infrastructure. For example, the network detection devices 104 may employ short-range communications protocols to emit and receive signals, for example containing specific header information to prompt the recording of a proximity event. The network detection devices 104 may therefore also generate network device proximity data including network detection device identifiers of the two nearby devices, as well as a timestamp indicating the date and time of the proximity event. For example, the network detection devices 104-1 and 104-3 may be in sufficiently close proximity to register a network device proximity event. Accordingly, one or both of the network detection devices 104-1 and 104-3 may obtain the network detection device identifier of the opposing device and generate network device proximity data The network detection devices 104 are configured to communicate with the network 108, which may be, for example, a cloud-based network of servers, repositories, and other computing devices which form a platform to provide network device data management, tracking and analysis at various facilities. The network 108 includes the network repository 112 and the server 116. In particular, the server 116 leverages contact tracing capabilities and functionalities of the tracing service network 124 to provide enhanced contact tracing at the network detection devices 104.

The network detection devices 104 transmit the device data, the account data, and the network device proximity data to the network repository 112 such as a data lake, where the data is stored for subsequent processing. The network detection devices 104 may communicate with the network repository 112 via one or more wired or wireless connections traversing one or more communications networks, including wide-area networks, such as the Internet. The network repository 112, therefore, collects data representing various environmental and operational characteristics captured within the facility. In other examples, different classes of network detection devices 104 may upload data objects to distinct repositories, or the network detection devices 104 may upload different classes of data objects to distinct repositories. The network repository 112 may further store device data, such as a static or base location of the network detection device 104 (i.e., identifying a facility that the network detection device 104 is located at), a type of the network detection device 104, or the like. The network repository 112 may further store operator data, such as operator names, contact information, and the like, associated with each operator identifier.

The system 100 also includes the server 116 connected to the network 108 and configured to access the repository 112 (or, as noted above, multiple repositories when relevant) via at least one application programming interface (API). In some examples, the repository 112 can be hosted at the server 116.

Figure 2:
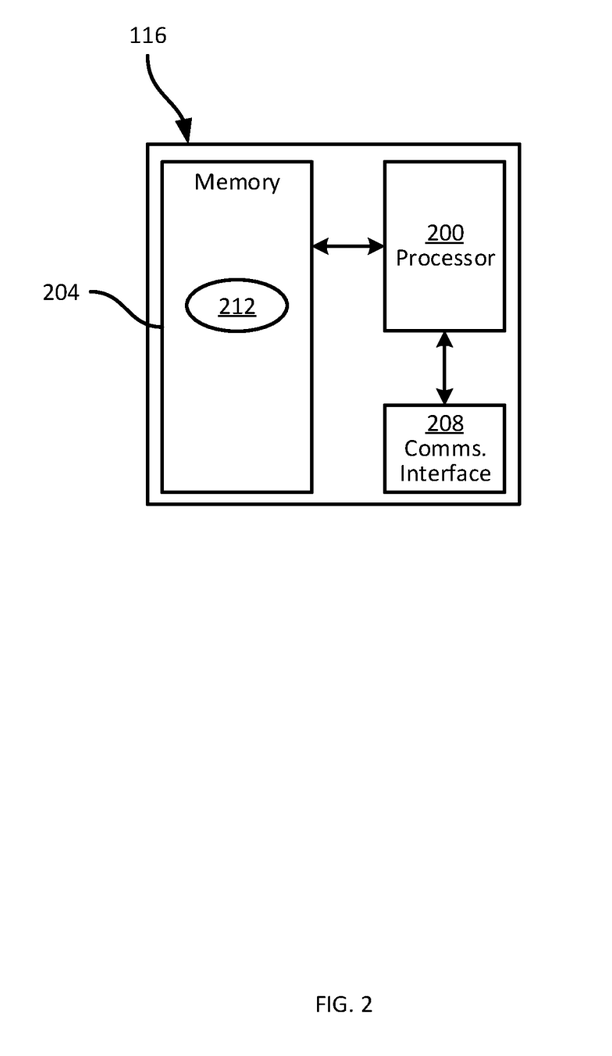
FIG. 2 is a block diagram of certain internal hardware components of the server of FIG. 1.

Turning to FIG. 2, certain internal components of the server 116 are illustrated. The server 116 includes a controller, such as a processor 200, interconnected with a non-transitory computer readable storage medium, such as a memory 204. The memory 204 includes a combination of volatile memory (e.g. Random Access Memory or RAM) and non-volatile memory (e.g. read only memory or ROM, Electrically Erasable Programmable Read Only Memory or EEPROM, flash memory). The processor 200 and the memory 204 each comprise one or more integrated circuits. The server 116 also includes a communications interface 208 enabling the server 116 to exchange data with other devices such as the repository 112 and the tracing service network 124.

The memory 204 stores computer readable instructions for execution by the processor 200. In particular, the memory 204 stores a contact tracing application 212 which, when executed by the processor 200, configures the processor 200 to determine facility exposure to the source condition and identify affected devices and operators. Those skilled in the art will appreciate that the functionality implemented by the processor 200 via the execution of the application 212 may also be implemented by one or more specially designed hardware and firmware components, such as FPGAs, ASICs and the like in other embodiments.

Returning to FIG. 1, the source device 120 may be a mobile computing device such as a mobile phone, tablet, or the like. The source device 120 is configured to execute a contact tracing application, such as the aforementioned Privacy-Preserving Exposure Notification. As will be discussed below in greater detail, the source device 120 acts as a beacon and emits encrypted proximity identifiers via a short-range wireless communication protocol (e.g., Bluetooth).

The network detection devices 104 are therefore also configured to detect short-range wireless communications, such as Bluetooth low energy signals emitted, for example, by the source device 120. In particular, the network detection devices 104 may detect a proximity identifier emitted by the source device 120 and generate proximity identifier data including the proximity identifier, a timestamp, the network detection device identifier, and the location of the network detection device 104.

The repository 112 therefore stores proximity identifier data including detected proximity identifiers, the associated network detection devices 104 that detected them, and timestamps and locations of detection. In some examples, the repository 112 may store the proximity identifier data on a rolling basis. That is, after a predefined storage period (e.g., 10 days, 2 weeks, 1 month, or a suitable time period corresponding, for example, to an incubation period of an infectious condition being tracked), the repository 112 may overwrite or otherwise delete the proximity identifier data.

The tracing service network 124 may, for example, another cloud-based network of servers, repositories and other computing devices which form a platform to provide a contact tracing service. The source device 120 may be configured to communicate with the network 124, for example to provide information to the tracing service network 124 if the user of the source device 120 is identified as being infected with condition being tracked. The network 124 may further provide privacy-protected information about an infected individual to allow for contact tracing, as is described in further detail below.

Figure 3:
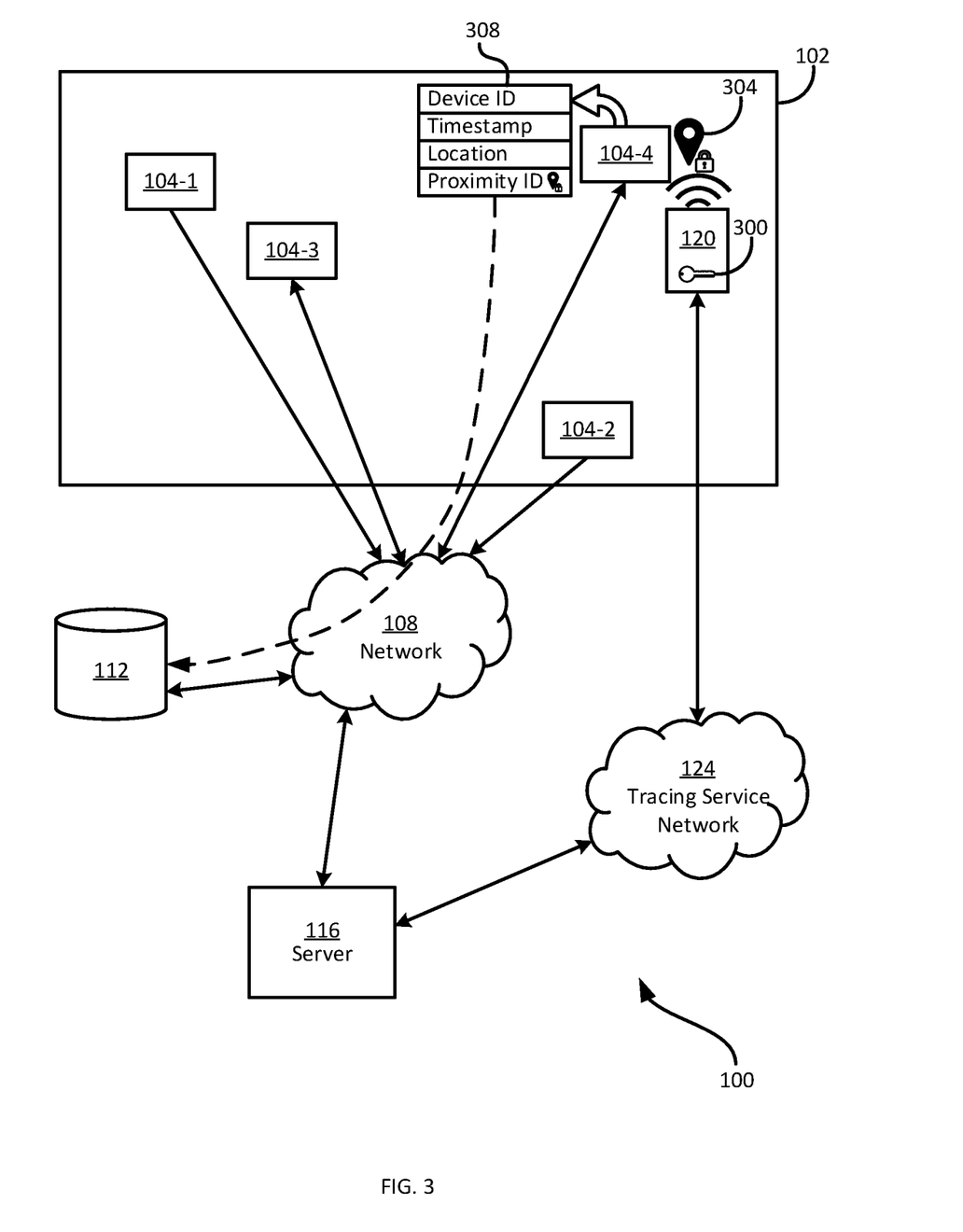
FIG. 3 is a schematic of data flow in the system of FIG. 1.

For example, referring to FIG. 3, a schematic of flow of data in the system 100 is depicted.

The source device 120 is associated with a key 300. The key 300 may be assigned or generated by the source device 120 or a control server on the tracing service network 124. The key 300 may be a unique one-time key, or it may be regenerated periodically (e.g., every 6 hours, every day, or other suitable period). The source device 120 uses the key 300 to generate a proximity identifier 304. For example, the key 300 may be used to encrypt a seed to generate the proximity identifier 304. The source device 120 may regenerate the proximity identifier 304 periodically (e.g., every 15 minutes, every hour, or other suitable period). The proximity identifier 304 may be identified by a specific header identifying the proximity identifier 304 as a contact tracing element. Specifically, by encrypting a seed using the key 300 to generate the proximity identifier 304, the publicly available proximity identifier 304 is anonymized.

The source device 120 is configured to act as a beacon and broadcast the current proximity identifier 304 via a short-range wireless communication protocol. Devices which are within a predetermined distance (e.g., 6 feet) may detect and record the proximity identifier 304. For example, the network detection device 104-4 detects the proximity identifier 304 and, in response, generates proximity identifier data 308 including a network detection device identifier of the network detection device 104-4, a timestamp of the date and time of detection of the proximity identifier 304, a location of the network detection device 104-4 at the time of detection of the proximity identifier 304, and the proximity identifier 304 itself. In some examples, the proximity identifier data 308 may only be recorded if the proximity identifier 304 is detected for a threshold period of time (e.g., 5 seconds, 30 seconds, or other suitable time period).

Having generated the proximity identifier data 308, the network detection device 104-4 is configured to transmit the proximity identifier data 308 to the network 108, and more particularly, to the repository 112 for storage and future processing.

In the event the user of the source device 120 is diagnosed as being infected with an infectious condition, the user may share the key 300 with the tracing service network 124. The tracing service network 124 may then publish the key 300 (referred to henceforth as the diagnosis key 300), for example by adding the diagnosis key 300 to a publicly accessible repository hosted at a server of the tracing service network 124.

To identify potential exposures, computing devices may periodically review the diagnosis keys published by the tracing service network 124. The computing devices may use cryptographic algorithms to determine associations between detected proximity identifiers and published diagnosis keys. For example, the computing devices may be configured to regenerate proximity keys generated using a diagnosis key in a predefined time period prior to the publication of the diagnosis key (i.e., to identify contacts of the user in an incubation period of the condition being tracked). In other examples, other manners of cryptographically associating the diagnosis key and the proximity identifiers may be employed, according to the cryptographic methods employed by the tracing service network 124 to preserve user anonymity.

Figure 4:
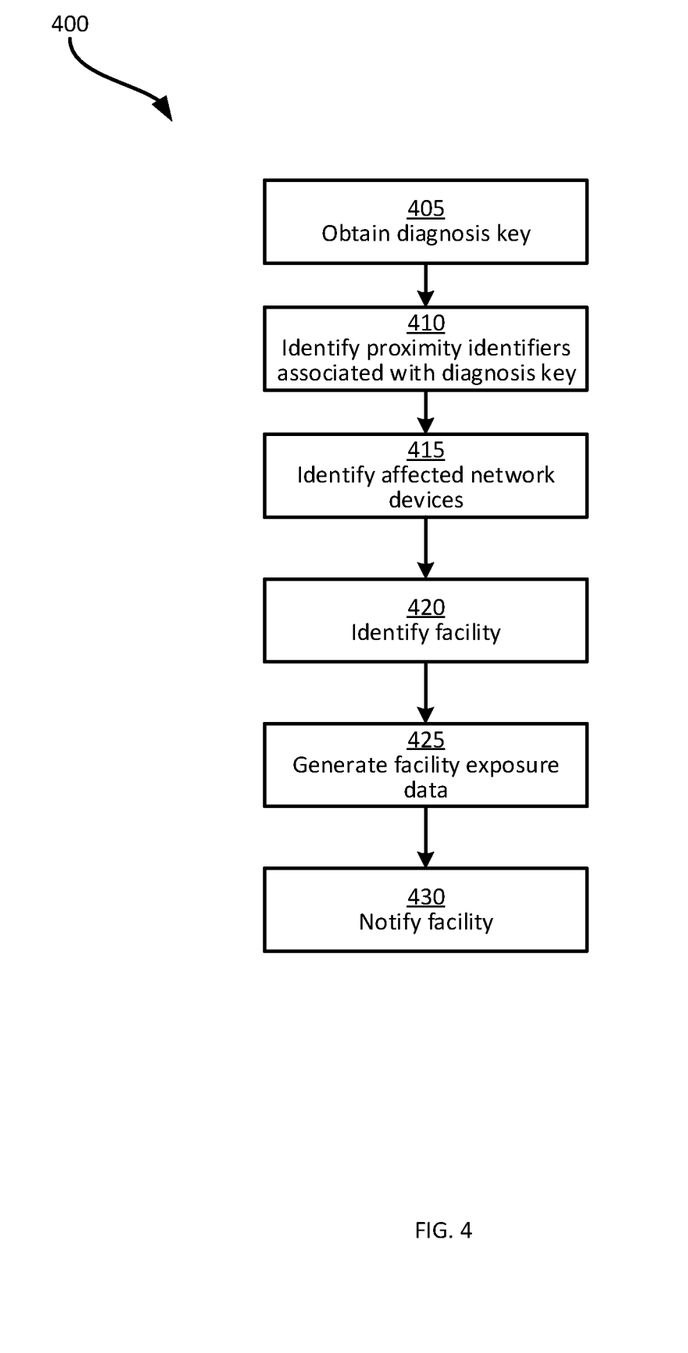
FIG. 4 is a flowchart of a method of determining facility exposure to a source condition.

Turning now to FIG. 4, the functionality implemented by the server 116 will be discussed in greater detail. FIG. 4 illustrates a method 400 of determining facility exposure to a source condition. The method 400 will be discussed in conjunction with its performance in the system 100, and particularly by the server 116, via execution of the application 212. In particular, the method 400 will be described with reference to the components of FIGS. 1, 2, and 3.

At block 405, the server 116 obtains diagnosis keys from the tracing service network 124. In the present example, the server 116 obtains the diagnosis key 300 from the tracing service network 124. For example, the server 116 may be configured to periodically scrape a diagnosis key repository hosted by the tracing service network 124.

At block 410, the server 116 identifies detected proximity identifiers, such as the proximity identifier 304, associated with the diagnosis key 300 obtained at block 405. That is, the server 116 determines whether the diagnosis key 300 is associated with any of the proximity identifiers detected by one of the network detection devices 104. For example, the server 116 may determine, from the diagnosis key 300, a set of source proximity identifiers issued by the source device over a predefined time period (e.g., 2 weeks prior to the diagnosis key 300 becoming available at the tracing service network 124). That is, the server 116 may regenerate the set of source proximity identifiers emitted by the source device 120, for example, based on known seeding algorithms and the diagnosis key 300. The server 116 may then compare the generated set of source proximity identifiers to detected proximity identifiers tracked in the proximity identifier data in the repository 112. In the present example, the server 116 may identify the proximity identifier 304 detected by the network detection device 104-4 in the proximity identifier data 308.

At block 415, the server 116 identifies one or more affected network detection devices 104 associated with the detected proximity identifiers identified at block 410. That is, the affected network detection devices may include the network detection devices 104 which detected the proximity identifiers identified at block 410. For example, the server 116 may retrieve the proximity identifier data containing the detected proximity identifiers identified at block 410 and extract the network detection device identifiers. In the present example, the server 116 may, in particular, retrieve the proximity identifier data 308 and extract the network detection device identifier of the network detection device 104-4.

At block 420, the server 116 identifies the facility or facilities of the affected network detection devices identified at block 415. Specifically, the server 116 may retrieve, from the repository 112, device data for the network detection device 104-4 to identify the facility 102 as being affected.

At block 425, the server 116 generates facility exposure data for the facility 102. The facility exposure data defines exposure associated with the source device 120 at the facility 102. For example, the facility exposure data may include identification of one or more affected operators (i.e., operators in close proximity to the user of the source device 120), an exposure window (i.e., a time period in which the source device 120 is determined to have been at the facility 102), or other data pertaining to exposure associated with the source device 120 at the facility 102. In some examples, the facility exposure data may further include subsequent facility-based contact tracing based on the affected operators.

To generate the facility exposure data, the server 116 may first obtain a set of affected network detection devices 104 associated with the facility 102. For example, the repository 112 may track network detection devices 104 across multiple facilities, and hence the affected network detection devices 104 identified at block 415 may include network detection devices 104 associated with different facilities. Having obtained the set of affected network detection devices 104 associated with a single facility, the server 116 may generate facility exposure data for said facility.

Figure 5:
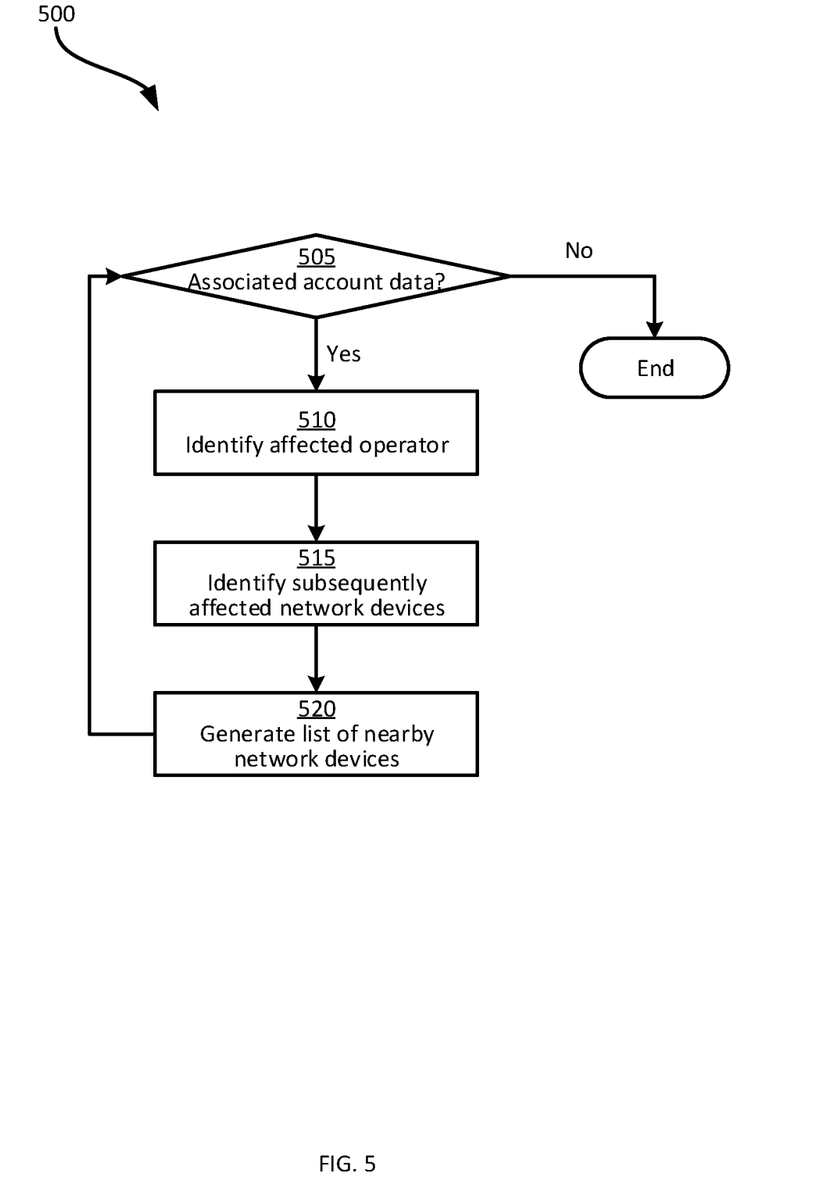
FIG. 5 is a flowchart of a method of generating facility exposure data at block 425 of the method of FIG. 4.

For example, referring to FIG. 5, an example method 500 of generating facility exposure data at block 425 is depicted. The method 500 is described in conjunction with its application to one of the affected network detection devices 104 associated with the facility 102. The method 500 may be repeated for each affected network detection device 104. In the present example, the method 500 is described based on its application to the network detection device 104-4.

At block 505, the server 116 determines whether account data is associated with the network detection device, for example, based on a type of the network detection device. For example, fixed sensors may not have an associated operator identifier, while computing devices, such as mobile computing devices, barcode scanners, or the like, may have an associated operator identifier indicating an operator using the network detection device.

If the determination at block 505 is negative, the method 500 ends.

If the determination at block 505 is affirmative, the server 116 proceeds to block 510. At block 510, the server 116 identifies an affected operator. For example, the server 116 may retrieve the account data associated with the network detection device 104-4 at the time the proximity identifier 304 was detected by the network detection device 104-4. That is, the server 116 identifies the operator using the network detection device 104-4 at the time the source device 120 was determined to be in close proximity to the network detection device 104-4. Specifically, the user of the source device 120 may have been in sufficiently close proximity to the operator of the network detection device 104-4 that the operator, also referred to as the affected operator, may have been infected and/or who may be required to take additional protective measures or precautions prior to diagnosis.

In some examples, the server 116 may be further configured to perform subsequent facility-based contact tracing based on the affected operators. In particular, at block 515, the server 116 may identify, based on the account data in the repository 112, subsequently affected network devices associated with the affected operator. For example, the server 116 may identify subsequently affected network detection devices 104 used by the affected operator on subsequent work shifts (i.e., subsequent to the affected operator having come into contact with the user of the source device 120).

At block 520, the server 116 generates a list of nearby network detection devices 104. That is, the server 116 may use the proximity of network detection devices 104 to identify subsequently affected operators, who may have come into contact with the affected operator identified at block 510. In the present example, the server 116 may retrieve the network device proximity data associated with the affected network device identified at block 415 of the method 400 and the subsequently affected network devices identified at block 515. More particularly, the server 116 may filter the network device proximity data for the affected network device based on the account data corresponding to the affected operator identified at block 510. That is, the server 116 may be configured to identify network detection devices in close proximity to the affected operator. The network detection devices 104 may also be identified as subsequently affected network detection devices.

Having identified additional subsequently affected network devices, the server 116 may return to block 505 for each subsequently affected network device on the list generated at block 520 to continue the facility-based contact tracing.

Figure 6:
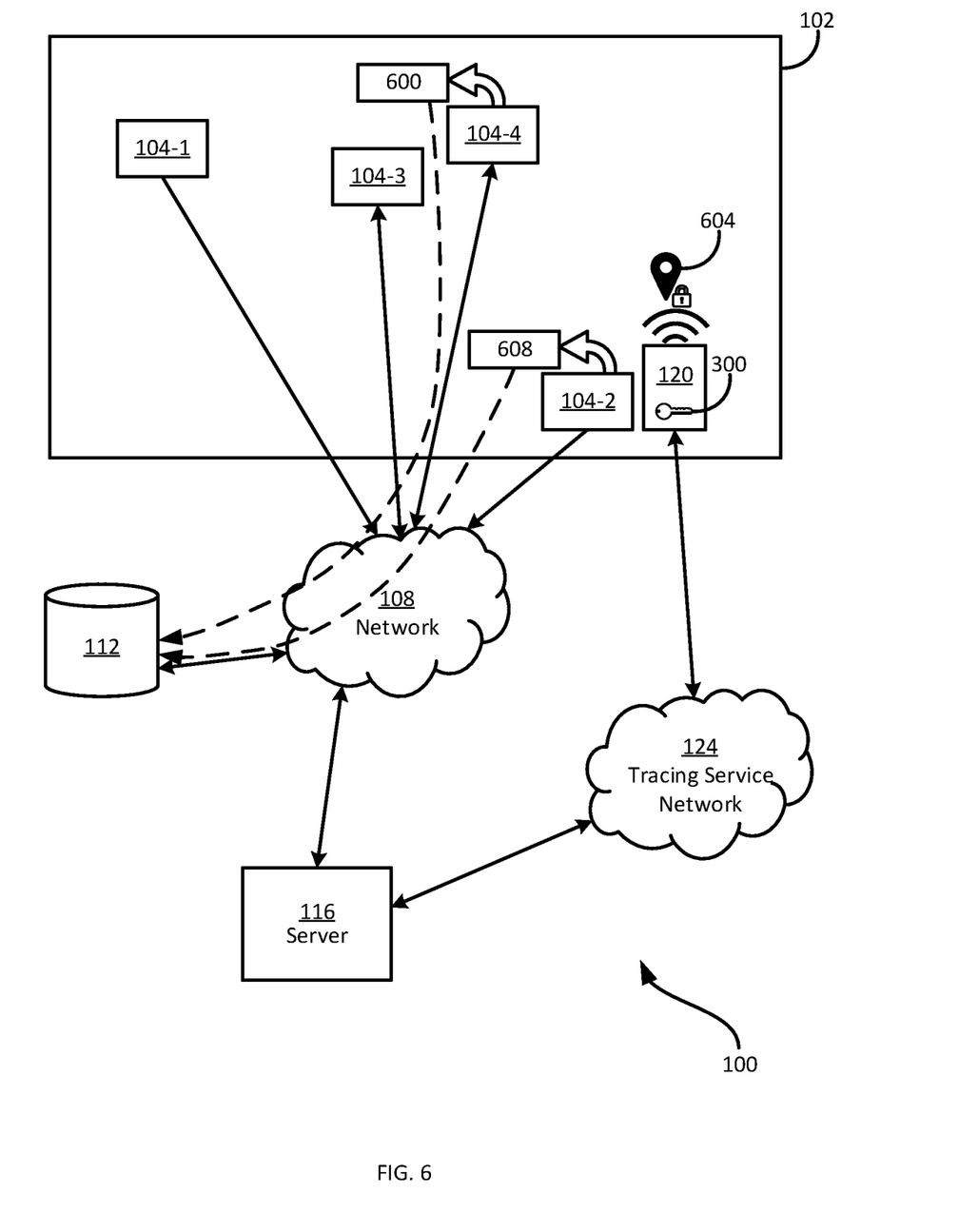
FIG. 6 is a schematic of further data flow in the system of FIG. 1.

For example, referring to FIG. 6, after having been exposed to the user of the source device 120, the operator of the network detection device 104-4 may come into close proximity with the operator of the network detection device 104-3 (e.g., to assist with a work task, for a lunch break, or the like). Accordingly, one or both of the network detection devices 104-3 and 104-4 may generate network device proximity data 600 and send that to the repository 112. Accordingly, at block 520, when performing facility-based contact tracing for the operator associated with the network detection device 104-4, the server 116 may identify the network detection device 104-3 as a subsequently affected network detection device. The server 116 may further execute the method 500 again to identify the operator of the network detection device 104-3 as a subsequently affected operator.

Figure 7:
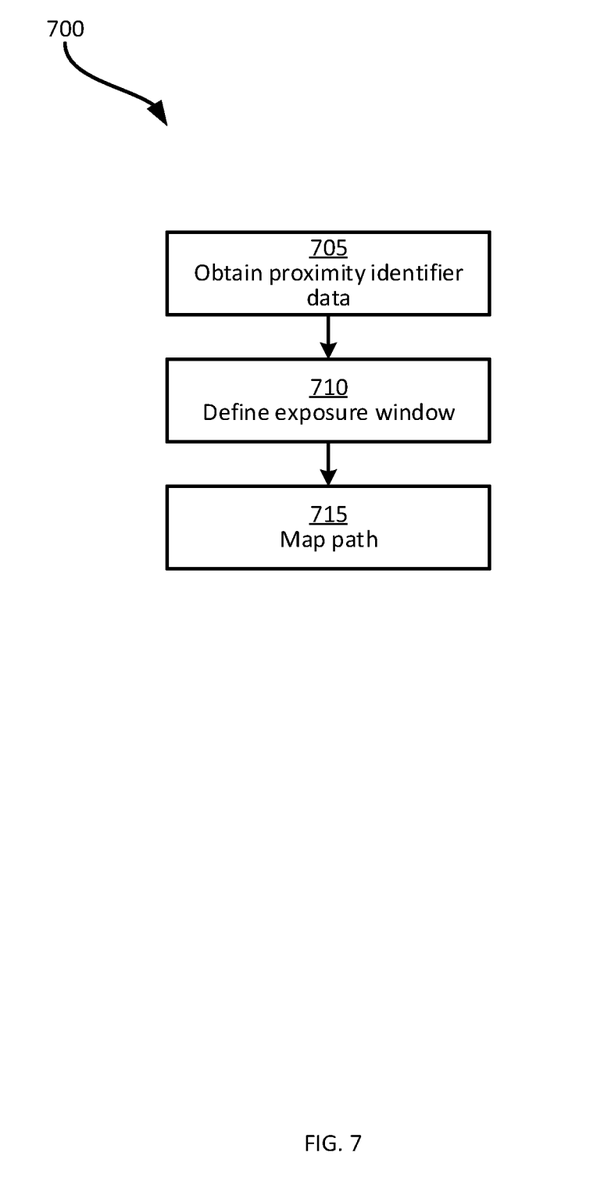
FIG. 7 is a flowchart of another method of generating facility exposure data at block 425 of the method of FIG. 4.

Turning to FIG. 7, another example method 700 of generating facility exposure data is depicted. In particular, the server 116 may execute the method 700 to define an exposure window at the facility 102, and to map a path of the source device 120 in the facility 102. That is, the server 116 may determine a time period in which the source device 120 is determined to have been at the facility 102.

At block 705, the server 116 obtain the proximity identifier data for proximity identifier detection events associated with the diagnosis key 300. Specifically, the proximity identifier detection events represent detections of a proximity identifier associated with the diagnosis key 300 by network detection devices 104. The proximity identifier data obtained by the server 116 may include the detected proximity identifier, the network detection device identifier of the network detection device 104 which detected the proximity identifier, a time of detection of the detected proximity identifier, and a location of the network detection device 104 which detected the proximity identifier at the time of detection.

At block 710, the server 116 defines the exposure window at the facility according to the timestamps defined in the proximity identifier data. In particular, the server 116 may identify, based on the proximity identifier data obtained at block 705, an earliest timestamp of a detected proximity identifier, and a latest timestamp of a detected proximity identifier to define the exposure window.

At block 715, the server 116 may map a path of the source device 120 in the facility 102 according to the proximity identifier data. For example, the server 116 may plot the detected proximity identifiers according to the location of the detecting network detection devices 104. By connecting the plotted proximity identifiers according to the timestamp of detection, the server 116 may generate an approximate path of the source device 120, as detectable by the network detection device infrastructure, in the facility 102.

For example, referring again to FIG. 6, the user of the source device 120 may move in a direction towards the network detection device 104-2. The source device 120 may continue emitting a proximity identifier 604, which may be different from the proximity identifier 304, if, for example, sufficient time has passed for the source device 120 to generate a new proximity identifier based on the key 300. The network detection device 104-2 may detect the proximity identifier 604 and generate and transmit proximity identifier data 608 to the repository 112 for storage and further processing.

Accordingly, at block 710, the server 116 may define the exposure window based on the timestamp defined in the proximity identifier data 308 and the timestamp defined in the proximity identifier data 608. At block 715, the server 116 may plot a path from the location defined in the proximity identifier data 308 at the timestamp defined in the proximity identifier data 308 to the location defined in the proximity identifier data 608 at the timestamp defined in the proximity identifier data 608.

Returning to FIG. 4, at block 430, the server 116 provides a notification of the facility exposure data at the facility 102. For example, the server 116 may send a message (e.g., an email or the like) or generate an alert for personnel at the facility 102. In some examples, the notification may include specific details regarding the affected operators and affected network detection devices. In other examples, the notification about specific affected operators may be provided directly to the affected operators (e.g., based on operator data stored at the repository 112).

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

The invention claimed is:

1. A method comprising:
   obtaining, at a server, a diagnosis key published by a tracing service, the diagnosis key associated with a source device;
   identifying one or more detected proximity identifiers associated with the diagnosis key;
   identifying one or more affected network detection devices associated with the one or more detected proximity identifiers;
   retrieving, from a repository, device data for the one or more affected network devices, the device data identifying a facility of the one or more affected network devices;
   generating facility exposure data for the facility, the facility exposure data defining exposure associated with the source device at the facility.

2. The method of claim 1, wherein generating facility exposure data comprises:
   retrieving, from the repository, account data for at least one of the one or more affected network devices; and
   identifying, based on the account data, an affected operator associated with the at least one affected network device.

3. The method of claim 2, wherein generating facility exposure data further comprises:
   retrieving, from the repository, network device proximity data for the at least one affected network device;
   identifying, based on the network device proximity data, identifying subsequently affected network devices;
   retrieving, from the repository, further account data for the subsequently affected network devices; and
   identifying, based on the further account data, subsequently affected operators associated with the subsequently affected network devices.

4. The method of claim 2, wherein generating facility exposure data further comprises identifying, based on the account data, subsequently affected network devices associated with the affected operator.

5. The method of claim 1, wherein generating facility exposure data comprises:
   retrieving, from the repository, proximity identifier data for the one or more detected proximity identifiers associated with the diagnosis key;
   defining an exposure window at the facility according to the proximity identifier data.

6. The method of claim 1, wherein generating facility exposure data comprises:
   retrieving, from the repository, proximity identifier data for the one or more detected proximity identifiers associated with the diagnosis key;
   mapping a path of the source device in the facility according to the proximity identifier data.

7. The method of claim 1, wherein identifying one or more detected proximity identifiers associated with the diagnosis key comprises:
   determining, from the diagnosis key, a set of source proximity identifiers issued by the source device over a predefined time period; and
   comparing the set of source proximity identifiers to detected proximity identifiers stored at the repository, to identify the one or more detected proximity identifiers.

8. The method of claim 1, further comprising providing a notification of the facility exposure data at the facility.

9. A server comprising:
   a memory; and
   a processor connected with the memory, the processor configured to:
   obtain a diagnosis key published by a tracing service, the diagnosis key associated with a source device;
   identify one or more detected proximity identifiers associated with the diagnosis key;
   identify one or more affected network detection devices associated with the one or more detected proximity identifiers;
   retrieve, from a repository connected to the server, device data for the one or more affected network devices, the device data identifying a facility of the one or more affected network devices;
   generate facility exposure data for the facility, the facility exposure data defining exposure associated with the source device at the facility.

10. The server of claim 9, wherein, to generate facility exposure data, the processor is configured to:
    retrieve, from the repository, account data for at least one of the one or more affected network devices; and
    identify, based on the account data, an affected operator associated with the at least one affected network device.

11. The server of claim 10, wherein, to generate facility exposure data, the processor is further configured to:
    retrieve, from the repository, network device proximity data for the at least one affected network device;
    identify, based on the network device proximity data, identifying subsequently affected network devices;
    retrieve, from the repository, further account data for the subsequently affected network devices; and
    identify, based on the further account data, subsequently affected operators associated with the subsequently affected network devices.

12. The server of claim 10, wherein, to generate facility exposure data, the processor is further configured to identify, based on the account data, subsequently affected network devices associated with the affected operator.

13. The server of claim 9, wherein, to generate facility exposure data, the processor is configured to:
    retrieve, from the repository, proximity identifier data for the one or more detected proximity identifiers associated with the diagnosis key;
    define an exposure window at the facility according to the proximity identifier data.

14. The server of claim 9, wherein, to generate facility exposure data, the processor is configured to:
  retrieve, from the repository, proximity identifier data for the one or more detected proximity identifiers associated with the diagnosis key;
  map a path of the source device in the facility according to the proximity identifier data.

15. The server of claim 9, wherein, to identify the one or more detected proximity identifiers associated with the diagnosis key, the processor is configured to:
  determining, from the diagnosis key, a set of source proximity identifiers issued by the source device over a predefined time period; and
  comparing the set of source proximity identifiers to detected proximity identifiers stored at the repository, to identify the one or more detected proximity identifiers.

16. The server of claim 9, wherein the processor is further configured to provide a notification of the facility exposure data at the facility.

17. A non-transitory computer-readable medium storing a plurality of computer-readable instructions executable by a processor, wherein execution of the instructions configures the processor to:
  obtain a diagnosis key published by a tracing service, the diagnosis key associated with a source device;
  identify one or more detected proximity identifiers associated with the diagnosis key;
  identify one or more affected network detection devices associated with the one or more detected proximity identifiers;
  retrieve, from a repository connected to the server, device data for the one or more affected network devices, the device data identifying a facility of the one or more affected network devices;
  generate facility exposure data for the facility, the facility exposure data defining exposure associated with the source device at the facility.

18. The non-transitory computer-readable medium of claim 17, wherein, to generate facility exposure data, execution of the instructions configures the processor to:
  retrieve, from the repository, account data for at least one of the one or more affected network devices; and
  identify, based on the account data, an affected operator associated with the at least one affected network device.

19. The non-transitory computer-readable medium of claim 18, wherein, to generate facility exposure data, execution of the instructions further configures the processor to:
  retrieve, from the repository, network device proximity data for the at least one affected network device;
  identify, based on the network device proximity data, identifying subsequently affected network devices;
  retrieve, from the repository, further account data for the subsequently affected network devices; and
  identify, based on the further account data, subsequently affected operators associated with the subsequently affected network devices.

20. The non-transitory computer-readable medium of claim 17, wherein, to generate facility exposure data, execution of the instructions configures the processor to:
  retrieve, from the repository, proximity identifier data for the one or more detected proximity identifiers associated with the diagnosis key;
  define an exposure window at the facility according to the proximity identifier data; and
  map a path of the source device in the facility according to the proximity identifier data.

* * * * *